US008454567B2

(12) United States Patent
Long et al.

(10) Patent No.: US 8,454,567 B2
(45) Date of Patent: Jun. 4, 2013

(54) MULTI-CONDUIT CONNECTORS AND METHODS FOR NEGATIVE PRESSURE WOUND THERAPY

(75) Inventors: Justin Alexander Long, San Antonio, TX (US); Aidan Marcus Tout, Alderbury (GB); Larry Tab Randolph, San Antonio, TX (US); Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 69 days.

(21) Appl. No.: 13/017,857

(22) Filed: Jan. 31, 2011

(65) Prior Publication Data

US 2011/0190717 A1    Aug. 4, 2011

Related U.S. Application Data

(60) Provisional application No. 61/300,362, filed on Feb. 1, 2010.

(51) Int. Cl.
| | |
|---|---|
| *A61M 1/00* | (2006.01) |
| *B65D 55/00* | (2006.01) |
| *B65D 51/00* | (2006.01) |
| *B65D 41/00* | (2006.01) |
| *B65D 43/00* | (2006.01) |
| *B65D 53/00* | (2006.01) |

(52) U.S. Cl.
USPC ........... 604/319; 604/317; 604/321; 604/322; 137/602; 137/603; 137/605; 137/606; 137/607; 137/888; 137/898; 215/306; 215/307; 215/308; 215/309; 215/316; 215/321; 215/322; 215/341; 215/342; 215/343; 220/255; 220/255.1; 220/256.1; 220/257.1; 220/257.2; 220/258.1; 220/258.2; 220/258.3; 220/258.4; 220/258.5; 220/259.1; 220/259.2; 220/259.3; 220/259.4; 220/259.5; 220/275; 222/519; 222/520; 222/521; 222/522; 222/523; 222/524; 222/525

(58) Field of Classification Search
None
See application file for complete search history.

(56) References Cited

U.S. PATENT DOCUMENTS

| | | | | |
|---|---|---|---|---|
| 4,804,366 | A | 2/1989 | Zdeb et al. | 604/85 |
| 4,850,978 | A | 7/1989 | Dudar et al. | 604/201 |
| 5,685,842 | A | 11/1997 | Drivas et al. | 604/500 |
| 6,957,779 | B2 | 10/2005 | Joshi et al. | 239/43 |
| 7,153,294 | B1 * | 12/2006 | Farrow | 604/319 |
| 2010/0106116 | A1 * | 4/2010 | Simmons et al. | 604/319 |

OTHER PUBLICATIONS

International Search Report and Written Opinion, issued in International Patent Application No. PCT/US2011/022571, mailed on Oct. 20, 2011.

* cited by examiner

*Primary Examiner* — Melanie Hand
*Assistant Examiner* — Joshua Lee

(57) ABSTRACT

Multi-conduit connector apparatuses for use in negative pressure wound therapy (NPWT) apparatuses to wound dressing, and methods for installing multi-conduit connector apparatuses in NPWT apparatuses.

17 Claims, 4 Drawing Sheets

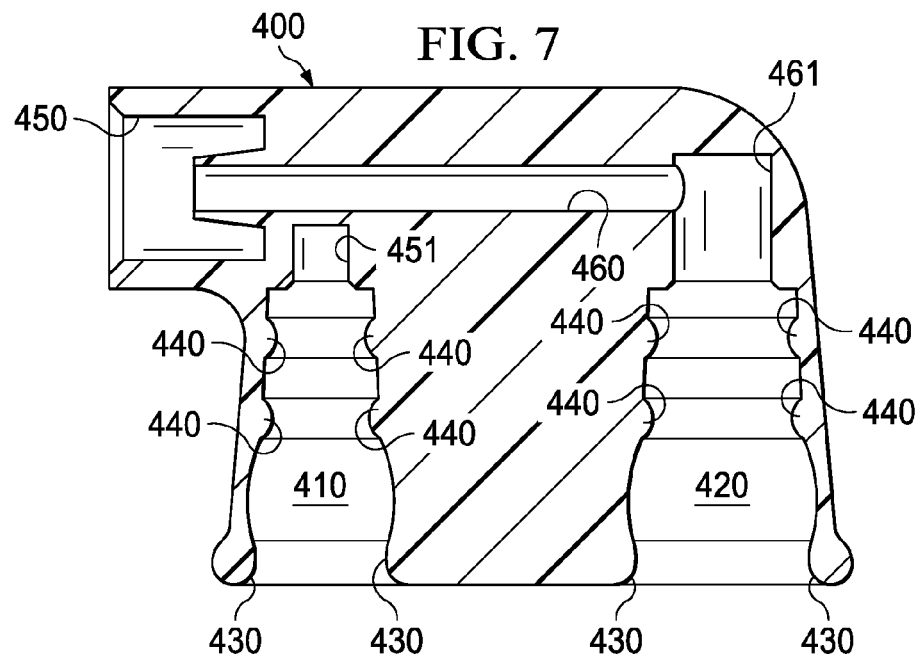
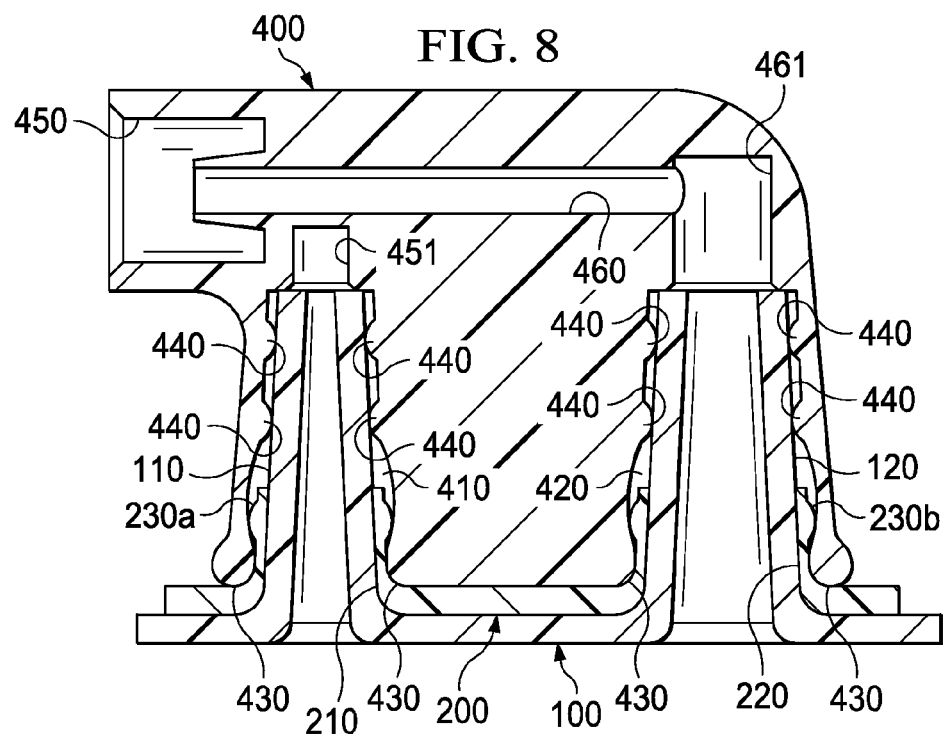

MULTI-CONDUIT CONNECTORS AND METHODS FOR NEGATIVE PRESSURE WOUND THERAPY

CROSS-REFERENCE(S) TO RELATED APPLICATION(S)

This application claims priority to U.S. Provisional Patent Application Ser. No. 61/300,362 filed Feb. 1, 2010. This provisional application is expressly incorporated by reference.

BACKGROUND

1. Field of the Invention

The present invention relates generally to healing of wounds and wound-treatment therapies. More particularly, but not by way of limitation, the present invention relates to apparatuses and methods for a multi-conduit connector used in negative pressure wound therapy (NPWT) apparatuses and methods.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device).

While NPWT has been highly successful in the promotion of wound closure, healing many wounds previously thought largely untreatable, some difficulty remains. One common component of an NPWT system is a device or structure (e.g., a multi-conduit connector) that connects a canister housing a vacuum, a fluid receptacle, or both to a medical tubeset. The tubeset may be used to deliver negative pressure to the wound site, to remove exudates from the wound site, or both.

While NPWT has been used for some time, multi-conduit connectors can be expensive to manufacture and difficult to install. Often, a user is unable to determine whether a connection has been made between the multi-conduit connector and the canister.

SUMMARY

The present disclosure includes embodiments of multi-conduit connectors. Specific embodiments comprise multi-conduit connector apparatuses for use in negative pressure wound therapy (NPWT) apparatuses and methods for installing multi-conduit connector apparatuses in NPWT apparatuses.

Specific embodiments include a multi-conduit connector apparatus comprising a canister lid comprising a first nipple and a second nipple; a cap sleeve, comprising a first annular sleeve and a second annular sleeve, where the first annular sleeve engages the first nipple and the second annular sleeve engages the second nipple; and a housing, comprising a first port, comprising a plurality of sealing ridges, the plurality of sealing ridges creating a seal with the first nipple; a second port, comprising a plurality of sealing ridges, the plurality of sealing ridges creating a seal with the second nipple; a first conduit comprising a first outlet, where the first outlet is in fluid communication with the first nipple; and a second conduit comprising a second outlet, where the second outlet is in fluid communication with the second nipple.

In certain embodiments, the first conduit is coupled to the first port. The second conduit may be coupled to the second port. The first conduit, the second conduit, or both may be coupled to a wound dressing. The first conduit and/or the second conduit may be comprised of a single lumen or multiple lumens.

Other embodiments may comprise a multi-conduit connector apparatus comprising: a canister lid comprising a first nipple and a second nipple; a cap sleeve, comprising: a first annular sleeve comprising a first clearance shoulder, where the first annular sleeve engages the first nipple; and a second annular sleeve comprising a second clearance shoulder, where the second annular sleeve engages the second nipple; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising a first outlet, where the first outlet is in fluid communication with the first nipple; and a second conduit comprising a second outlet, where the second outlet is in fluid communication with the second nipple.

In certain embodiments, the first outlet is coupled to the first nipple. In other embodiments, the second outlet is coupled to the second nipple. In specific embodiments, the first conduit or the second conduit may be coupled to a wound site. In some embodiments, the first nipple or the second nipple may be a tapered nipple.

In some embodiments, the cap sleeve may further comprises a sleeve lid and/or a hinge. The cap sleeve lid may be comprised of plastic or rubber in certain embodiments.

In certain embodiments, the clearance shoulder is substantially a ring. In other embodiments, the clearance shoulder is deformable.

Still other embodiments comprise a multi-conduit connector apparatus comprising: a canister lid comprising a first nipple and a second nipple, where the first nipple further comprises a first clearance shoulder, and the second nipple further comprises a second clearance shoulder; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising: a first outlet, where the first outlet is coupled to the first nipple, and where the multi-lumen coupling member is configured to be coupled to a wound site; and a second conduit comprising: a second outlet, where the second outlet is coupled to the second nipple, and where the second conduit member is configured to be coupled to a wound site.

Other embodiments may comprise obtaining a multi-conduit connector apparatus comprising: a canister lid comprising a first nipple and a second nipple; a cap sleeve, comprising: a first annular sleeve comprising a first clearance shoulder, where the first annular sleeve engages the first nipple; and a second annular sleeve comprising a second clearance shoulder, where the second annular sleeve engages the second nipple; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising a first outlet, where the first outlet is in fluid communication with the first nipple; and a second conduit comprising a second outlet, where the second outlet is in fluid communication with the second nipple; placing the cap sleeve on the canister lid; placing the housing on the cap sleeve and canister lid; and applying a downward force until the housing has fully engaged the canister lid. Still other embodiments comprise placing the housing on the cap sleeve and the canister lid and applying a downward force to the housing until the housing has fully engaged the canister lid.

Yet other embodiments comprise a method for sealing a multi conduit connector, comprising: obtaining a multi-conduit connector apparatus comprising: a canister lid comprising a first nipple and a second nipple, where the first nipple further comprises a first clearance shoulder, and the second nipple further comprises a second clearance shoulder; and a housing, comprising: a first port, comprising: a plurality of sealing ridges, the plurality of sealing ridges creating a seal with the first nipple; and a first engagement tab, the first engagement tab engaging the first clearance shoulder; a second port, comprising: a plurality of sealing ridges, the plurality of sealing ridges creating a seal with the second nipple; and a second engagement tab, the second engagement tab engaging the second clearance shoulder; a first conduit comprising: a first outlet, where the first outlet is coupled to the first nipple, and where the multi-lumen coupling member is configured to be coupled to a wound site; and a second conduit comprising: a second outlet, where the second outlet is coupled to the second nipple, and where the second conduit member is configured to be coupled to a wound site; placing the housing of on the canister lid; and applying a downward force until the housing has fully engaged the canister lid.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears, and structural features may be drawn larger or smaller than scale. Identical reference numbers do not necessarily indicate an identical structure. Rather, the same reference number may be used to indicate a similar feature or a feature with similar functionality, as may non-identical reference numbers.

FIG. 7 depicts a cross-sectional view of one embodiment of the multi-conduit housing.

FIG. 8 depicts a cross-sectional assembly view of the canister lid of FIG. 3, the cap sleeve of FIG. 4 and the multi-conduit housing of FIG. 6.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a connector that "comprises," "has," "includes" or "contains" one or more elements possesses those one or more elements, but is not limited to possessing only those elements. For example, in a connector that comprises a nipple and a port, the connector includes the specified elements but is not limited to having only those elements. For example, such a connector could also include an annular sleeve.

Further, a device or structure that is configured in a certain way is configured in at least that way, but it can also be configured in other ways than those specifically described.

Embodiments of the multi-conduit connector apparatus depicted may be used in a variety of applications. A non-limiting example of a use for a multi-conduit connector apparatus is in the field of negative pressure wound therapy (NPWT). The connector apparatus can link more than one conduit to a wound dressing and a wound treatment apparatus.

Figure 1:
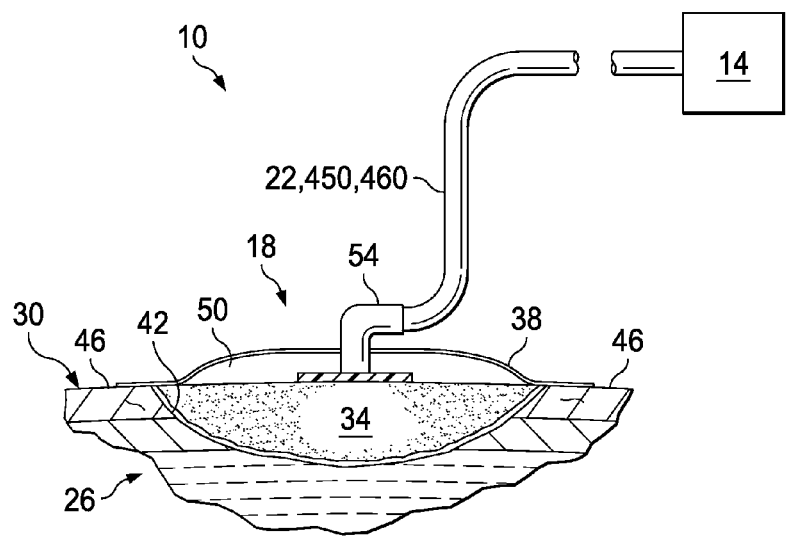
FIG. 1 depicts a schematic view of a wound treatment system.

FIG. 1 shows an embodiment of a wound treatment system 10. In the embodiment shown, apparatus 10 comprises a wound-treatment apparatus 14, and a wound dressing 18 coupled to apparatus 14 by a conduit 22. In the embodiment shown, conduit 22 further comprises a conduit 450 and a conduit 460. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (for example, an instillation fluid such as a medicinal fluid, antibacterial fluid, or an irrigation fluid) to wound dressing 18. Wound treatment apparatus 14 may further comprise multi-conduit connector apparatus 1000 depicted in FIG. 2 and FIG. 3. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduits 22, 450, 460 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduits 22, 450, 460 can comprise, for example, multiple lumens (e.g., as in a single conduit with a central limit for application of negative pressure and/or fluid delivery and one or more peripheral lumens disposed adjacent or around the central lumen such that the peripheral lumens can be coupled to a pressure sensor to sense and/or detect a pressure or negative pressure between drape 38 and surface 42 (e.g. in space 50), as described in the Hunt and Boynton patents incorporated above.

In the embodiment shown, system 10 further comprises a wound dressing connection pad 54 configured to be coupled (and shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
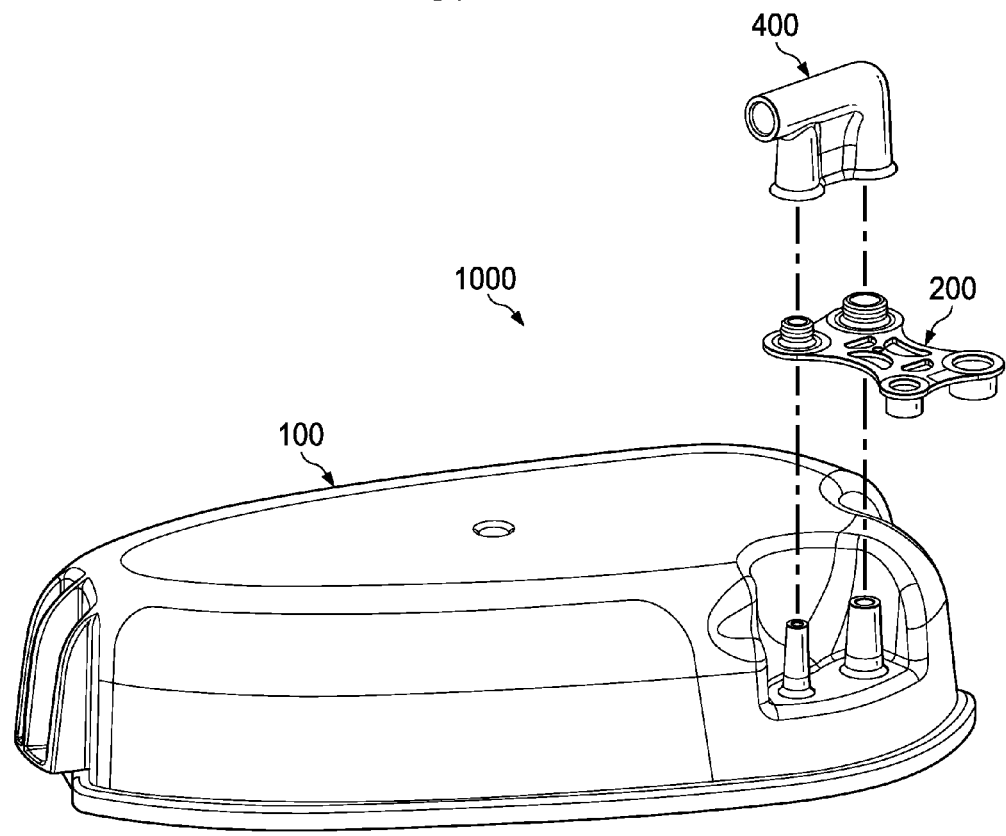
FIG. 2 depicts an exploded view of one embodiment of the present multi-conduit connector, canister lid, cap sleeve, and multi-conduit housing.
Figure 3:
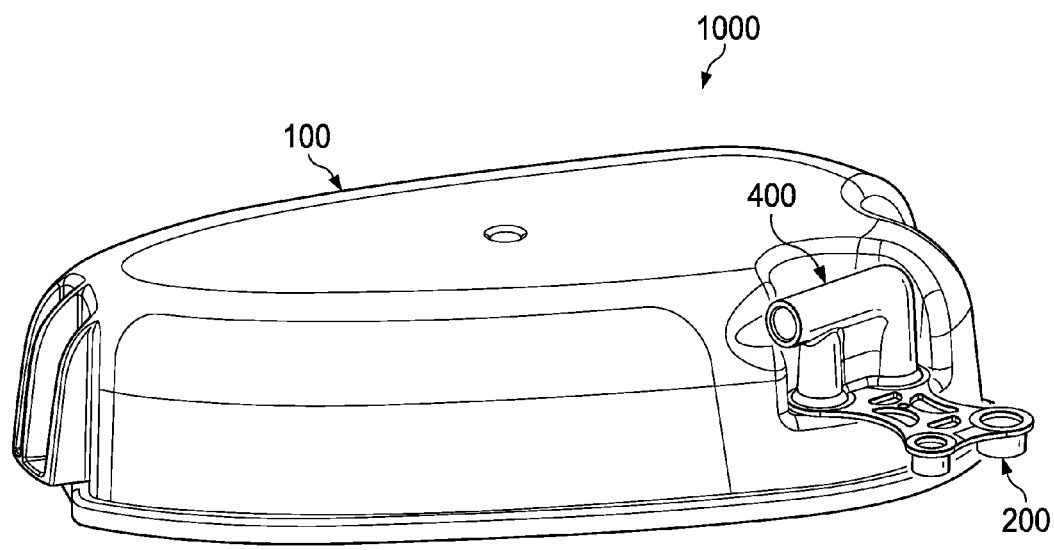
FIG. 3 depicts an assembly view of the multi-conduit connector, canister lid, cap sleeve, and multi-conduit housing.

Turning now to FIG. 2 and FIG. 3, one example of a multi-conduit connector apparatus 1000 is shown that comprises embodiments of a canister lid 100, a cap sleeve 200, and a multi-conduit housing 400 is shown. FIG. 2 shows an exploded view, while FIG. 3 shows an assembly view in which canister lid 100, cap sleeve 200, and multi-conduit housing 400 are coupled together. In the embodiment shown, cap sleeve 200 is placed over nipples 110, 120 on canister lid 100. Multi conduit housing 400 is placed over canister lid 100 and cap sleeve 200.

In some embodiments, canister lid 100, cap sleeve 200, and/or multi-conduit housing 400 may be comprised of rubber or plastic. In some embodiments, canister lid 100, cap sleeve 200, and multi-conduit housing 400 may be designed for a single use.

Figure 4:
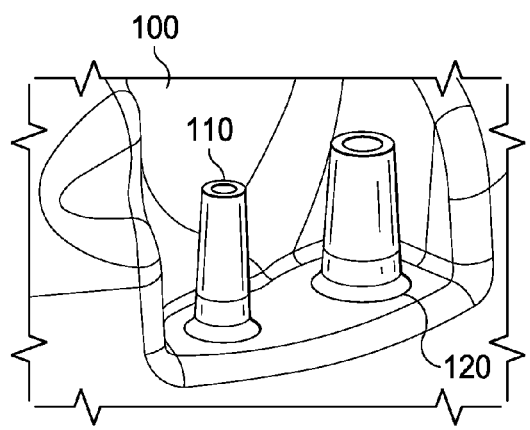
FIG. 4 depicts a perspective view of a portion of the canister lid of FIGS. 2 and 3.

Referring now to FIG. 4, an example of a canister lid 100 is shown. Other features of a canister lid not relating to the embodiments of the invention disclosed are not pictured for the sake of clarity. Canister lid 100 comprises first nipple 110 and second nipple 120. First nipple 110 may be configured to be coupled to a first outlet 451 shown in FIG. 7. Second nipple 120 may be configured to be coupled to an second outlet 461 shown in FIG. 7.

In some embodiments, first nipple 110 is configured to be coupled to a vacuum pump, a pressure sensor, or both. In some embodiments, second nipple 120 is configured to be coupled to an exudate receptacle. In other embodiments second nipple 120 is configured to be coupled to a source of medicaments.

Figure 5:
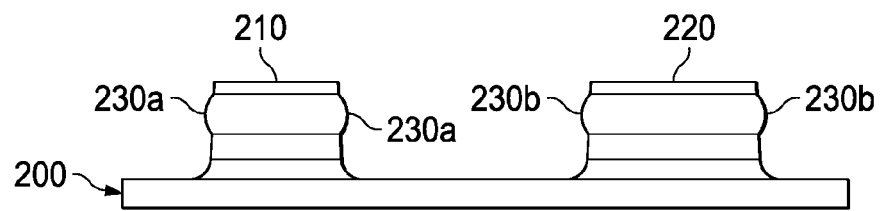
FIG. 5 depicts a side view of one embodiment of the present cap sleeve.

Referring now to FIG. 5, an example of a cap sleeve 200 is shown. Cap sleeve 200 comprises a first annular sleeve 210 and a second annular sleeve 220. First annular sleeve 210 and second annular sleeve 220 comprises a first clearance shoulder 230a on the outer surface of the sleeve. Second annular sleeve 220 comprises a second clearance shoulder 230b on the outer surface of the sleeve. Some embodiments of cap sleeve 200 may comprise a hinge and a lid (not shown) for each annular sleeve 210, 220 coupled to the hinge. Other embodiments may have a separate lid piece (not shown) for the annular sleeves 210, 220.

Figure 6:
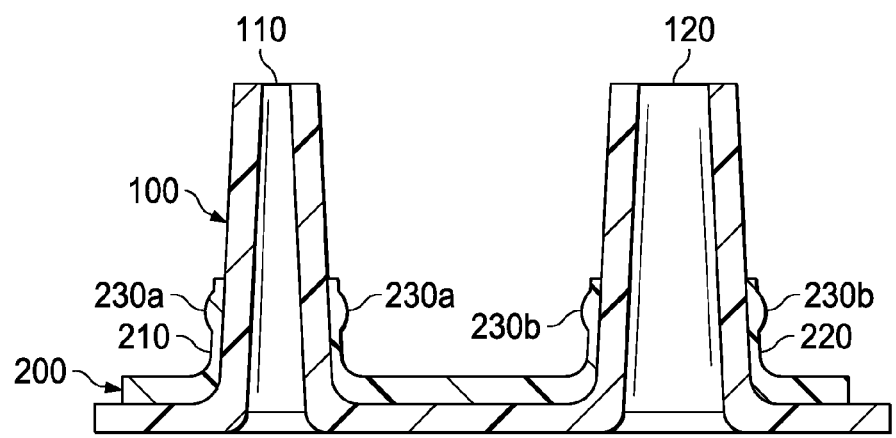
FIG. 6 depicts a side cross-sectional view of the cap sleeve of FIG. 5 coupled to the portion of the canister lid of FIG. 4.

Referring now to FIG. 6, a sectional assembly view of canister lid 100 of FIG. 4 and cap sleeve 200 of FIG. 5 is shown. Cap sleeve 200 is coupled to canister lid 100. In some embodiments, cap sleeve 200 may be removably coupled to canister lid 100. In other embodiments, cap sleeve 200 may be permanently affixed to canister lid 100. First annular sleeve 210 engages first nipple 110. Second annular sleeve 220 engages second nipple 120. Annular sleeves 210, 220 may be substantially in the shape of a circular ring in some embodiments. In other embodiments, annular sleeves 210, 220 may be substantially in the shape of a triangular ring, a square ring, or any other ring shape.

Referring now to FIG. 7, a sectional view of multi-conduit housing 400 is shown. Multi-conduit housing 400 comprises a first port 410 and a second port 420. First port 410 is configured to engage first nipple 110. Second port 420 is configured to engage second nipple 120. First port 410 comprises engagement tab 430 and a plurality of sealing ridges 440. Second port 420 comprises engagement tab 430 and a plurality of sealing ridges 440. Engagement tabs 430 are configured to engage clearance shoulders 230a, 230b. Sealing ridges 440 are configured to engage first nipple 110 and second nipple 120. In some embodiments, engagement tab 430 and sealing ridges 440 are made of a deformable material, including but not limited to rubber or plastic.

Ports 410, 420 are structural elements of multi-conduit housing 400 that are configured to be coupled to nipples 110, 120. Ports 410, 420 are substantially the inverse shape of the corresponding nipples 110, 120. For example, in some embodiments nipples 110, 120 are substantially in the shape of a frustum. In these embodiments, corresponding ports 410, 420 are also in the shape of a frustum. Nipples 110, 120 and ports 410, 420 may also be in the shape of cylinders, cones, prisms, or any other shape about which a seal can be created.

Multi-conduit housing 400 further comprises a first conduit 450 and a second conduit 460. First conduit 450 is configured to be coupled to a wound site. Multi-conduit housing 400 further comprises a first outlet 451. In some embodiments, first outlet 451 is configured to be coupled to first nipple 110. First conduit 450 is in fluid communication with first outlet 451.

Second conduit 460 is configured to be coupled to a wound site and further comprises a second outlet 461. In some embodiments, second outlet 461 is configured to be coupled to second nipple 120. First conduit 450 and second conduit 460 may be coaxial or parallel. Second conduit 460 is in fluid communication with second outlet 461.

Referring now to FIG. 8, a sectional assembly view of canister lid 100, cap sleeve 200, and multi-conduit housing 400 of FIG. 3 is shown. Cap sleeve 200 is coupled to canister lid 100. In some embodiments, cap sleeve 200 may be removably coupled to canister lid 100. In other embodiments, cap sleeve 200 may be permanently affixed to canister lid 100. First annular sleeve 210 engages first nipple 110. Second annular sleeve 220 engages second nipple 120.

Multi-conduit housing 400 engages both cap sleeve 200 and canister lid 100. First port 410 engages first nipple 110. First outlet 451 is in fluid communication with first nipple 110. Second port 420 engages second nipple 120. Second outlet 461 is in fluid communication with second nipple 120.

Engagement tab 430 engages clearance shoulders 230*a*, 230*b*, creating a seal between first port 410 and first annular sleeve 210, and also creating a seal between second port 420 and second annular sleeve 220. Sealing ridges 440 engage first nipple 110, creating a seal between first port 410 and first nipple 110. Sealing ridges 440 also engage second nipple 120, creating a seal between second port 420 and second nipple 120.

Other embodiments of this disclosure comprise only canister lid 100 and multi-conduit housing 400. First nipple 110 further comprises first clearance shoulder 230*a*. Second nipple 120 also further comprises second clearance shoulder 230*b*.

The arrangement in FIG. 8 provides a user with tactile and audible feedback that a connection has been made. In some embodiments, cap sleeve 200 is coupled to canister lid 100 during the manufacturing process. In other embodiments, cap sleeve 200 is installed by a user. In a hospital or clinical setting, a user may engage multi-conduit housing 400 with first nipple 110 and second nipple 120. The user may apply a downward force to multi-conduit housing 400 until engagement tabs 430 passes clearance shoulders 230*a*, 230*b* and can move no further. In some embodiments, an audible sound may be heard once multi-conduit housing 400 is fully engaged.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of this invention.

We claim:

1. A multi-conduit connector apparatus comprising:
 a canister lid comprising a first nipple and a second nipple;
 a cap sleeve, comprising:
  a first annular sleeve comprising a first clearance shoulder, where the first annular sleeve engages the first nipple; and
  a second annular sleeve comprising a second clearance shoulder, where the second annular sleeve engages the second nipple; and
 a housing, comprising:
  a first port, comprising:
   a plurality of sealing ridges, the plurality of sealing ridges creating a seal with the first nipple; and
   a first engagement tab, the first engagement tab engaging the first clearance shoulder;
  a second port, comprising:
   a plurality of sealing ridges, the plurality of sealing ridges creating a seal with the second nipple; and
   a second engagement tab, the second engagement tab engaging the second clearance shoulder;
 a first conduit comprising a first outlet, where the first outlet is in fluid communication with the first nipple; and
 a second conduit comprising a second outlet, where the second outlet is in fluid communication with the second nipple.

2. The apparatus of claim 1, where the first outlet is coupled to the first nipple.

3. The apparatus of claim 1, where the second outlet is coupled to the second nipple.

4. The apparatus of claim 1, where the first conduit is coupled to a wound site.

5. The apparatus of claim 1, where the second conduit is coupled to a wound site.

6. The apparatus of claim 1, where the first nipple is a tapered nipple.

7. The apparatus of claim 1, where the second nipple is a tapered nipple.

8. The apparatus of claim 1, where the cap sleeve further comprises a sleeve lid.

9. The apparatus of claim 8, where the cap sleeve further comprises a hinge.

10. The apparatus of claim 1, where the cap sleeve is further comprised of plastic.

11. The apparatus of claim 1, where the cap sleeve is further comprised of rubber.

12. The apparatus of claim 1, where the clearance shoulder is substantially a ring.

13. The apparatus of claim 1, where the clearance shoulder is deformable.

14. A multi-conduit connector apparatus comprising:
 a canister lid comprising a first nipple and a second nipple, where the first nipple further comprises a first clearance shoulder, and the second nipple further comprises a second clearance shoulder; and
 a housing, comprising:
  a first port, comprising:
   a plurality of sealing ridges, the plurality of sealing ridges creating a seal with the first nipple; and
   a first engagement tab, the first engagement tab engaging the first clearance shoulder;
  a second port, comprising:
   a plurality of sealing ridges, the plurality of sealing ridges creating a seal with the second nipple; and
   a second engagement tab, the second engagement tab engaging the second clearance shoulder;
 a first conduit comprising a first outlet, where the first outlet is coupled to the first nipple, and where the multi-lumen coupling member is configured to be coupled to a wound site; and a second conduit comprising a second outlet, where the second outlet is coupled to the second nipple, and where the second conduit member is configured to be coupled to a wound site.

15. A method for sealing a multi-conduit connector, comprising:
   obtaining:
      a canister lid comprising a first nipple and a second nipple;
      a cap sleeve, comprising:
         a first annular sleeve comprising a first clearance shoulder, where the first annular sleeve engages the first nipple; and
         a second annular sleeve comprising a second clearance shoulder, where the second annular sleeve engages the second nipple; and
      a housing, comprising:
         a first port, comprising:
            a plurality of sealing ridges, the plurality of sealing ridges creating a seal with the first nipple; and
            a first engagement tab, the first engagement tab engaging the first clearance shoulder;
         a second port, comprising:
            a plurality of sealing ridges, the plurality of sealing ridges creating a seal with the second nipple; and
            a second engagement tab, the second engagement tab engaging the second clearance shoulder;
   placing the cap sleeve on the canister lid;
   placing the housing on the cap sleeve and canister lid; and
   applying a downward force to the housing until the housing has fully engaged the canister lid.

16. A method for sealing a multi-conduit connector, comprising:
   obtaining:
      a canister lid comprising a first nipple and a second nipple;
      a cap sleeve, comprising:
         a first annular sleeve comprising a first clearance shoulder, where the first annular sleeve engages the first nipple; and
         a second annular sleeve comprising a second clearance shoulder, where the second annular sleeve engages the second nipple; and
      a housing, comprising
         a first port, comprising:
            a plurality of sealing ridges, the plurality of sealing ridges creating a seal with the first nipple; and
            a first engagement tab, the first engagement tab engaging the first clearance shoulder;
         a second port, comprising:
            a plurality of sealing ridges, the plurality of sealing ridges creating a seal with the second nipple; and
            a second engagement tab, the second engagement tab engaging the second clearance shoulder; and
   placing the housing on the cap sleeve and the canister lid and applying a downward force to the housing until the housing has fully engaged the canister lid.

17. A method for sealing a multi conduit connector, comprising:
   obtaining:
      a canister lid comprising a first nipple and a second nipple, where the first nipple further comprises a first clearance shoulder, and the second nipple further comprises a second clearance shoulder; and
      a housing, comprising:
         a first port, comprising:
            a plurality of sealing ridges, the plurality of sealing ridges creating a seal with the first nipple; and
            a first engagement tab, the first engagement tab engaging the first clearance shoulder;
         a second port, comprising:
            a plurality of sealing ridges, the plurality of sealing ridges creating a seal with the second nipple; and
            a second engagement tab, the second engagement tab engaging the second clearance shoulder;
   placing the housing on the canister lid; and
   applying a downward force until the housing has fully engaged the canister lid.

* * * * *